United States Patent
Stewart et al.

(10) Patent No.: US 9,662,319 B2
(45) Date of Patent: May 30, 2017

(54) METHODS AND MATERIALS FOR ASSESSING RESPONSIVENESS TO LENALIDOMIDE, THALIDOMIDE, AND/OR OTHER THALIDOMIDE ANALOGS

(75) Inventors: Alexander Keith Stewart, Scottsdale, AZ (US); Peter Bergsagel, Scottsdale, AZ (US); Rafael Fonseca, Scottsdale, AZ (US); Esteban Braggio, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 10 days.

(21) Appl. No.: 14/003,622

(22) PCT Filed: Mar. 8, 2012

(86) PCT No.: PCT/US2012/028285
§ 371 (c)(1),
(2), (4) Date: Nov. 18, 2013

(87) PCT Pub. No.: WO2012/125405
PCT Pub. Date: Sep. 20, 2012

(65) Prior Publication Data
US 2014/0066480 A1    Mar. 6, 2014

Related U.S. Application Data

(60) Provisional application No. 61/452,027, filed on Mar. 11, 2011.

(51) Int. Cl.
*A61K 31/454* (2006.01)
*G01N 33/574* (2006.01)

(52) U.S. Cl.
CPC ..... *A61K 31/454* (2013.01); *G01N 33/57426* (2013.01); *G01N 2800/52* (2013.01)

(58) Field of Classification Search
None
See application file for complete search history.

(56) References Cited

U.S. PATENT DOCUMENTS

2005/0256000 A1    11/2005   Schaper et al.

FOREIGN PATENT DOCUMENTS

| WO | 2010137547 | 2/2010 |
| WO | 2011020839 | 2/2011 |

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Fish & Richardson P.C.

(57) ABSTRACT

This document provides methods and materials related to assessing responsiveness to lenalidomide, thalidomide, and/or other IMiDs (structural and functional analogues of thalidomide that represent a promising new class of immunomodulators). For example, methods and materials for using CRBN levels to determine whether or not cancer cells (e.g., multiple myeloma cells) are susceptible to lenalidomide, thalidomide, and/or other IMiDs are provided.

7 Claims, 8 Drawing Sheets

List of genes shared in OPM1 cells after CRBN knockdown and Lenalidomide treatment

| Down-regulated | | | | Up-regulated | | |
|---|---|---|---|---|---|---|
| AGPS | GALNTL4 | PGM2 | TMEM33 | ADAT3 | HLA-DPB1 | RTP4 |
| AJAP1 | GINS4 | PPIF | TMEM64 | ATXN1 | HLA-DQA1 | SUMF1 |
| APTX | GNPNAT1 | PPP2R1B | TNFRSF21 | AUTS2 | HLA-DQA1 /// | TMEM185A |
| BCL11B | HAUS7 /// TREX2 | RAD18 | TRIM4 | BTBD7 | HLA-DRB1 /// HLA-DRB3 | UTRN |
| BEST3 | HINT3 | RFC3 | USP9X | C10orf10 | HLA-DRB1 /// HLA-DRB4 | WDFY3 |
| BID | HS3ST3B1 | RGS1 | WDR4 | C2orf68 | HLA-DRB1 /// HLA-DRB4 | |
| C12orf66 | ITPR1 | RGS16 | WDR72 | CARD16 | IFIH1 | |
| C13orf1 | LOC730631 | ROR1 | ZNF148 | CASP1 | IGF2BP3 | |
| C18orf54 | LOC84740 | RRP1B | ZNF561 | CTTNBP2 | LIMA1 | |
| C7orf68 | LPL | SEC24A | ZNF706 | DCC | LRRC4C | |
| CEP72 | LRRC8B | SEL1L | ZWILCH | DHTKD1 | MAML2 | |
| CNKSR2 | MMACHC | SETD7 | | DLEU2 | MARCH2 | |
| COX11 | MRS2 | SETMAR | | DNAJC5B | MB | |
| DFFA | MTAP | SLC7A2 | | ELF3 | NFIB | |
| DNAJC25 | MYB | SMCR7L | | EXTL2 | NMI | |
| DTNA | NEK6 | SMEK2 | | FCHO2 | PCBP2 | |
| EIF3M | NETO2 | SNHG3 | | GIMAP2 | PLOD2 | |
| FAM76B | NUDCD1 | SNRPN | | HIPK2 | PTEN | |
| FANCI | NUP43 | STAMBPL1 | | HIST1H2AD /// HIST1H3D | PTPRM | |
| FKBP11 | ORC5L | SUV39H2 | | HIST1H2BG | RASGRP3 | |
| FLJ25006 | PDK1 | TET1 | | HIST2H4A /// HIST2H4B | RCAN3 | |
| GABRB2 | | | | | | |

(56) References Cited

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Blade, Novel Drugs for the treatment of multiple myeloma, 2010, haematologica, 95(5), pp. 702-704.*
Ito, Identification of a Primary Target of Thalidomide Teratogenicity, 2010, Science, 327, pp. 1345-1350.*
International Search Report and Written Opinion in International Application No. PCT/US2012/028285, mailed Sep. 19, 2012, 5 pages.
International Preliminary Report on Patentability in International Application No. PCT/US2012/028285, issued Sep. 17, 2013, 5 pages.
Extended European Search Report in EP Application No. 12757445.7, dated Jan. 8, 2014, 4 pages.
Office Action in EP Application No. 12757445.7, dated Oct. 30, 2013, 2 pages.
Braggio et el., "Identification of copy number abnormalities and inactivating mutations in two negative regulators of nuclear factor-kappaB signaling pathways in Waldenstrom's macroglobulinemia," Cancer Res., 2009, 69(8):3579-88.
GenBank® Accession No. AAH17419.1, 2006, 2 pages.
GenBank® Accession No. AAH69905.1, 2004, 2 pages.
GenBank® Accession No. NC_009159.2, 2008, 1 page.
GenBank® Accession No. NG_016864.1, 2010, 11 pages.
GenBank® Accession No. NM_001195647.1, 2010, 2 pages.
GenBank® Accession No. NM_021449.2, 2010, 4 pages.
GenBank® Accession No. NP_001182576.1, 2010, 1 page.
GenBank® Accession No. XP_001496748.1, 2008, 1 page.
Ito et al., "Identification of a Primay Target of Thalidomide Teratogenicity," Science, Mar. 12, 2010. 327:1345-1350.
Ito et al., "Teratogenic effects of thalidomide: molecular mechanisms," Cell Mol Life Sci., Jan. 5, 2011, 68(9):1569-1579.
Lipson et al., "Efficient calculation of interval scores for DNA copy number data analysis," J. Comput. Biol., 2006, 13(2):215-28.
Zhu et al., "RNAi screen of the druggable genome identifies modulators of proteasome inhibitor sensitivity in myeloma including CDK5," Blood, 2011, 117(14):3847-3857.
Office Action in Australian Application No. 2012229333 issued Apr. 13, 2016, 3 pages.
Office Action in European Application No. 12757445.7, dated Jun. 12, 2015, 3 pages.

* cited by examiner

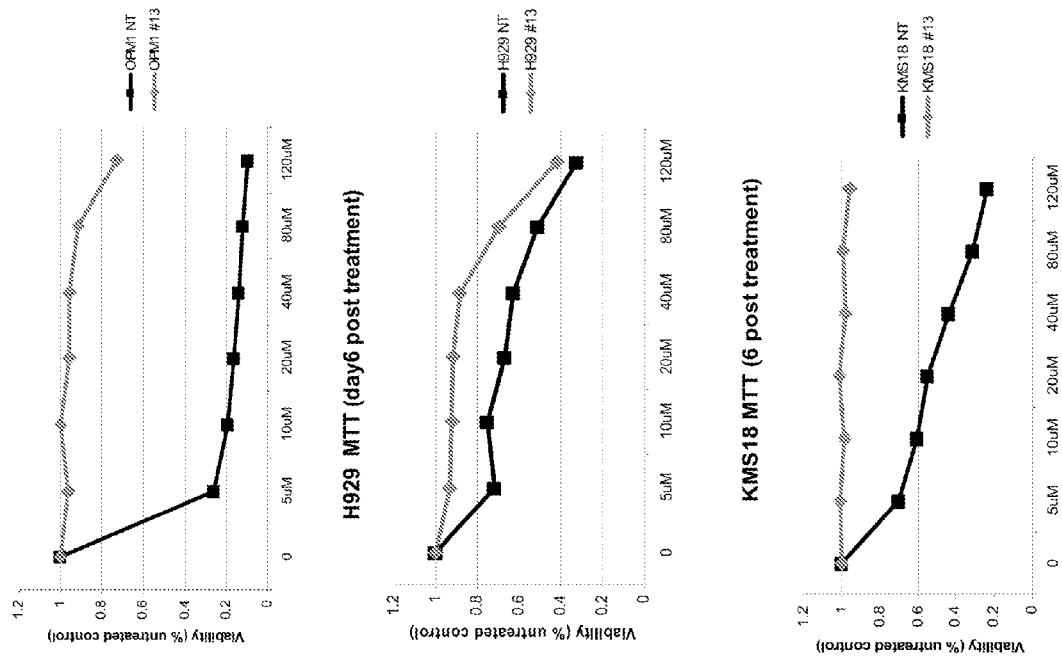
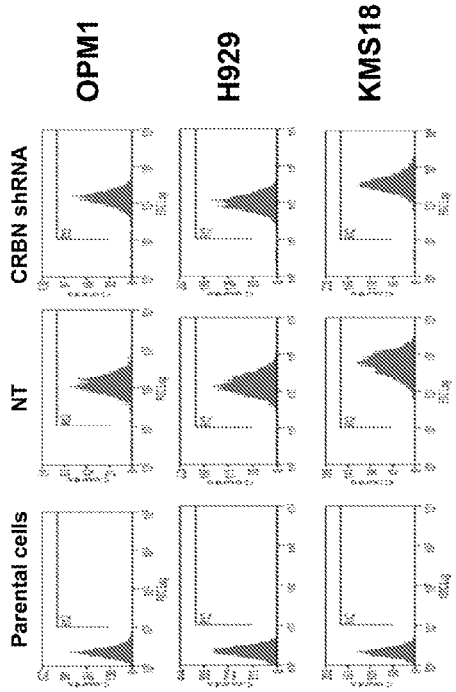
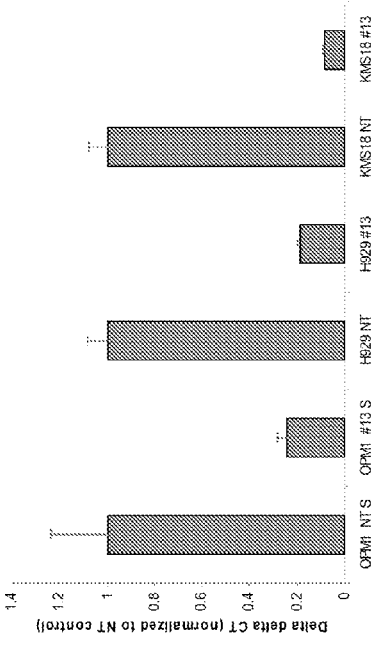
Figure 3

Figure 8: List of genes shared in OPM1 cells after CRBN knockdown and Lenalidomide treatment

| Down-regulated | | | | Up-regulated | | |
|---|---|---|---|---|---|---|
| AGPS | GALNTL4 | PGM2 | TMEM33 | ADAT3 | HLA-DPB1 | RTP4 |
| AJAP1 | GINS4 | PPIF | TMEM64 | ATXN1 | HLA-DQA1 | SUMF1 |
| APTX | GNPNAT1 | PPP2R1B | TNFRSF21 | AUTS2 | HLA-DQA1 /// | TMEM185A |
| BCL11B | HAUS7 /// TREX2 | RAD18 | TRIM4 | BTBD7 | HLA-DRB1 /// HLA-DRB3 | UTRN |
| BEST3 | HINT3 | RFC3 | USP9X | C10orf10 | HLA-DRB1 /// HLA-DRB4 | WDFY3 |
| BID | HS3ST3B1 | RGS1 | WDR4 | C2orf68 | HLA-DRB1 /// HLA-DRB4 | |
| C12orf66 | ITPR1 | RGS16 | WDR72 | CARD16 | IFIH1 | |
| C13orf1 | LOC730631 | ROR1 | ZNF148 | CASP1 | IGF2BP3 | |
| C18orf54 | LOC84740 | RRP1B | ZNF561 | CTTNBP2 | LIMA1 | |
| C7orf68 | LPL | SEC24A | ZNF706 | DCC | LRRC4C | |
| CEP72 | LRRC8B | SEL1L | ZWILCH | DHTKD1 | MAML2 | |
| CNKSR2 | MMACHC | SETD7 | | DLEU2 | MARCH2 | |
| COX11 | MRS2 | SETMAR | | DNAJC5B | MB | |
| DFFA | MTAP | SLC7A2 | | ELF3 | NFIB | |
| DNAJC25 | MYB | SMCR7L | | EXTL2 | NMI | |
| DTNA | NEK6 | SMEK2 | | FCHO2 | PCBP2 | |
| EIF3M | NETO2 | SNHG3 | | GIMAP2 | PLOD2 | |
| FAM76B | NUDCD1 | SNRPN | | HIPK2 | PTEN | |
| FANCI | NUP43 | STAMBPL1 | | HIST1H2AD /// HIST1H3D | PTPRM | |
| FKBP11 | ORC5L | SUV39H2 | | HIST1H2BG | RASGRP3 | |
| FLJ25006 | PDK1 | TET1 | | HIST2H4A /// HIST2H4B | RCAN3 | |
| GABRB2 | | | | | | |

METHODS AND MATERIALS FOR ASSESSING RESPONSIVENESS TO LENALIDOMIDE, THALIDOMIDE, AND/OR OTHER THALIDOMIDE ANALOGS

CROSS-REFERENCE TO RELATED APPLICATIONS

This application is a National Stage application under 35 U.S.C. §371 of International Application No. PCT/US2012/028285, having an International Filing Date of Mar. 8, 2012, which claims the benefit of U.S. Provisional Application Ser. No. 61/452,027, filed Mar. 11, 2011. The disclosure of the prior application is considered part of (and are incorporated by reference in) the disclosure of this application.

BACKGROUND

1. Technical Field

This document relates to methods and materials involved in assessing responsiveness to lenalidomide, thalidomide, and/or other IMiDs (structural and functional analogues of thalidomide that represent a promising new class of immunomodulators). For example, this document relates to methods and materials for using cereblon (CRBN) levels to determine whether or not cancer cells are susceptible to lenalidomide, thalidomide, and/or other IMiDs.

2. Background Information

Thalidomide was used a sedative in the late 1950s and later withdrawn from use due to its teratogenicity. Because of its antiangiogenic activity, thalidomide was recently used to treat multiple myeloma, but its overall mechanism of action is unknown.

SUMMARY

This document provides methods and materials related to assessing responsiveness to lenalidomide, thalidomide, and/or other IMiDs (structural and functional analogues of thalidomide that represent a promising new class of immunomodulators). Examples of IMiDs include, without limitation, lenalidomide and pomalidomide. For example, this document provides methods and materials for using CRBN levels to determine whether or not cancer cells (e.g., multiple myeloma cells) are susceptible to lenalidomide, thalidomide, and/or other IMiDs. As described herein, cancer cells (e.g., multiple myeloma cells) expressing CRBN are susceptible to treatment with lenalidomide, thalidomide, and/or other IMiDs, while cancer cells not expressing CRBN are not susceptible to treatment with lenalidomide, thalidomide, and/or other IMiDs.

Determining if a mammal (e.g., a human patient) has cancer cells expressing CRBN can allow physicians and the patient, in the case of humans, to determine a course of thalidomide and/or IMiDs treatment appropriate for that patient. For example, a patient found to have multiple myeloma cells expressing CRBN can be treated with lenalidomide, thalidomide, and/or other IMiDs. Likewise, determining if a mammal (e.g., a human patient) has cancer cells expressing little or no CRBN can allow physicians and the patient, in the case of humans, to determine a course of cancer treatment other than lenalidomide, thalidomide, and/or other IMiDs. For example, a patient found to have multiple myeloma cells not expressing CRBN can be treated with Bortezomib, alkylating agents, or corticosteroids.

In some cases, the methods and materials provided herein can be used to monitor a patient's cancer progression and/or treatment course over time. For example, a patient's cancer cells (e.g., multiple myeloma cells) can be assessed for CRBN levels before treatment starts and at various time points following the initiation of treatment. If CRBN expression levels drop in the patient's cancer cells, then the patient can be switched from a lenalidomide, thalidomide, and/or other IMiDs treatment to a treatment other than thalidomide and IMiDs. If the patient's cancer cells remain positive for CRBN expression, then the patient can continue to be treated with lenalidomide, thalidomide, and/or other IMiDs.

In general, one aspect of this document features a method for assessing responsiveness to a thalidomide or thalidomide analog treatment. The method comprises, or consists essentially of, (a) determining whether or not cancer cells from a mammal express CRBN, (b) classifying the cancer cells as being susceptible to treatment with thalidomide or a thalidomide analog if the cancer cells express CRBN, and (c) classifying the mammal as not being susceptible to treatment with thalidomide or a thalidomide analog if the cancer cells do not express CRBN. The cancer cells can be multiple myeloma cells. The mammal can be a human. The determining step can comprise determining whether or not the cancer cells express CRBN mRNA. The determining step can comprise determining whether or not the cancer cells express CRBN polypeptides. The method can comprise assessing responsiveness to the thalidomide analog treatment, wherein the thalidomide analog treatment can be a lenalidomide treatment, and wherein the thalidomide analog can be lenalidomide.

In another aspect, this document features a method for assessing responsiveness to a thalidomide or thalidomide analog treatment. The method comprises, or consists essentially of, (a) determining whether or not cancer cells from a mammal comprise an elevated level of CRBN expression, (b) classifying the cancer cells as being susceptible to treatment with thalidomide or a thalidomide analog if the cancer cells comprise the elevated level, and (c) classifying the mammal as not being susceptible to treatment with thalidomide or a thalidomide analog if the cancer cells do not comprise the elevated level. The cancer cells can be multiple myeloma cells. The mammal can be a human. The CRBN expression can be CRBN mRNA expression. The CRBN expression can be CRBN polypeptide expression. The method can comprise assessing responsiveness to the thalidomide analog treatment, wherein the thalidomide analog treatment can be a lenalidomide treatment, and wherein the thalidomide analog can be lenalidomide.

In another aspect, this document features a method for identifying cancer cells susceptible to treatment with thalidomide or a thalidomide analog, wherein the method comprises, or consists essentially of, (a) detecting the presence of CRBN expression by cancer cells, and (b) classifying the cancer cells as being susceptible to treatment with thalidomide or a thalidomide analog based at least in part on the presence. The cancer cells can be multiple myeloma cells. The CRBN expression can be CRBN mRNA expression. The CRBN expression can be CRBN polypeptide expression. The method can comprise identifying cancer cells susceptible to treatment with the thalidomide analog, and wherein the thalidomide analog can be lenalidomide.

In another aspect, this document features a method for identifying cancer cells susceptible to treatment with thalidomide or a thalidomide analog, wherein the method comprises, or consists essentially of, (a) detecting the presence of an elevated level of CRBN expression by cancer cells, and (b) classifying the cancer cells as being susceptible to treatment with thalidomide or a thalidomide analog based at least in part on the presence. The cancer cells can be multiple myeloma cells. The CRBN expression can be CRBN mRNA expression. The CRBN expression can be CRBN polypeptide expression. The method can comprise identifying cancer cells susceptible to treatment with the thalidomide analog, and wherein the thalidomide analog can be lenalidomide.

In another aspect, this document features a method for monitoring treatment with a thalidomide or thalidomide analog, wherein the method comprises, or consists essentially of, (a) determining whether or not cancer cells obtained from a mammal treated with the thalidomide or thalidomide analog express CRBN, (b) classifying the cancer cells as being susceptible to treatment with thalidomide or a thalidomide analog if the cancer cells express CRBN, and (c) classifying the mammal as not being susceptible to treatment with thalidomide or a thalidomide analog if the cancer cells do not express CRBN. The method can comprise monitoring treatment with the thalidomide analog, and wherein the thalidomide analog can be lenalidomide.

In another aspect, this document features a method for monitoring treatment with a thalidomide or thalidomide analog, wherein the method comprises, or consists essentially of, (a) administering thalidomide or a thalidomide analog to a mammal having cancer cells that express CRBN, (b) determining whether or not cancer cells obtained from the mammal continue to express CRBN, (c) administering thalidomide or a thalidomide analog to the mammal if the cancer cells continue to express CRBN, and (d) administering a treatment other than thalidomide or a thalidomide analog to the mammal if the cancer cells do not continue to express CRBN. The method can comprise monitoring treatment with the thalidomide analog, and wherein the thalidomide analog can be lenalidomide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3A contains graphs plotting the percentage of GFP from the indicated cell lines containing non-targeting control shRNA (NT) or an shRNA designed to reduce CRBN expression (CRBN shRNA). Each shRNA construct included a sequence encoding GFP. FIG. 3B is a graph plotting RT-PCR for CRBN expression in the indicated cell lines containing non-targeting control shRNA (NT) or shRNA #13. FIG. 3C contains graphs plotting cell viability for the indicated cells lines containing either a non-targeting control shRNA (NT) or shRNA #13 and treated with the indicated amount of lenalidomide.

FIG. 8 is a list of up-regulated and down-regulated genes that are shared in OPM1 cells after CRBN knockdown and OPM1 cells after lenalidomide treatment.

DETAILED DESCRIPTION

Figure 1:
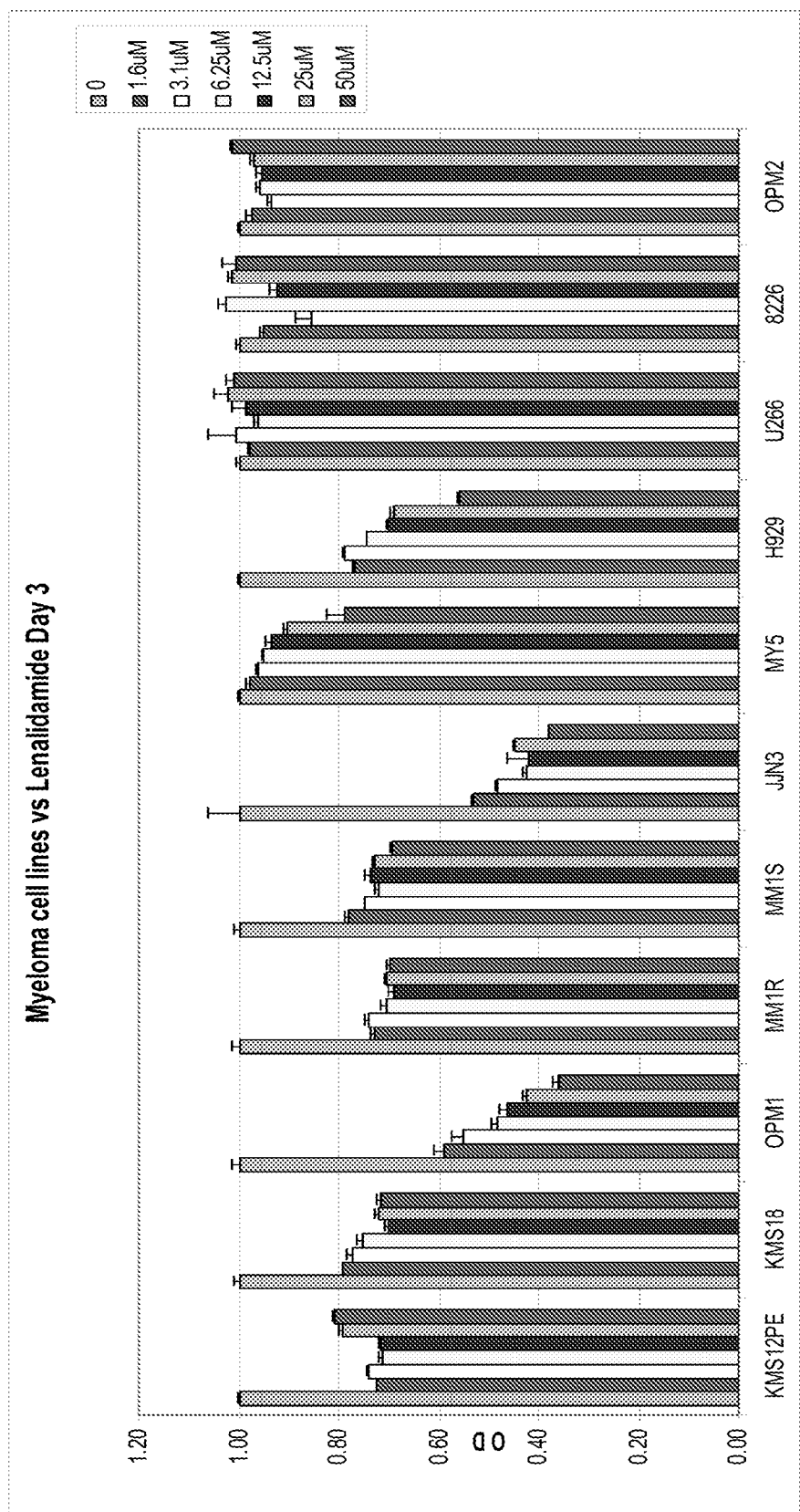
FIG. 1 is a graph plotting the viability of the indicated cell lines treated with 0, 1.6, 3.1, 6.25, 12.5, 25, and 50 µM of lenalidomide for 72 hours.

This document provides methods and materials related to assessing responsiveness to lenalidomide, thalidomide, and/or other IMiDs. For example, this document provides methods and materials for using CRBN levels to determine whether or not cancer cells (e.g., multiple myeloma cells) are susceptible to lenalidomide, thalidomide, and/or other IMiDs. As described herein, cancer cells (e.g., multiple myeloma cells) expressing CRBN are susceptible to treatment with lenalidomide, thalidomide, and/or other IMiDs, while cancer cells not expressing CRBN are not susceptible to treatment with lenalidomide, thalidomide, and/or other IMiDs.

Any appropriate cancer cell can be assessed for CRBN expression to determine if it is susceptible to treatment with lenalidomide, thalidomide, and/or other IMiDs. For example, multiple myeloma cells, lymphoma cells, chronic lymphocytic leukemia cells, myelodysplasia cells, and other blood cancer cells can be assessed for CRBN expression to determine if such cells are susceptible to treatment with lenalidomide, thalidomide, and/or other IMiDs. In addition, the methods and materials provided herein can be used to assess cancer cells from any appropriate mammal For example, cancer cells from a human, monkey, horse, dog, cat, cow, pig, mouse, or rat can be assessed for CRBN expression to determine if the cancer cells are susceptible to treatment with lenalidomide, thalidomide, and/or other IMiDs.

The amino acid sequence of a human CRBN polypeptide is set forth in GenBank® GI No. 16924279 (GenBank® Accession No. AAH17419.1), and the nucleic acid sequence encoding a human CRBN polypeptide is set forth in GenBank® GI No. 292658851 (GenBank® Accession No. NG_01684.1). The amino acid sequence of a monkey CRBN polypeptide is set forth in GenBank® GI No. 307548871 (GenBank® Accession No. NP_001182576.1), and the nucleic acid sequence encoding a monkey CRBN polypeptide is set forth in GenBank® GI No. 307548870 (GenBank® Accession No. NM_001195647.1). The amino acid sequence of a horse CRBN polypeptide is set forth in GenBank® GI No. 149728337 (GenBank® Accession No. XP_001496748.1), and the nucleic acid sequence encoding a horse CRBN polypeptide is set forth in GenBank® GI No. 194246364 (GenBank® Accession No. NC_009159.2). The amino acid sequence of a mouse CRBN polypeptide is set forth in GenBank® GI No. 47682727 (GenBank® Accession No. AAH69905.1), and the nucleic acid sequence encoding a mouse CRBN polypeptide is set forth in GenBank® GI No. 90403611 (GenBank® Accession No. NM_021449.2). Additional amino acid and nucleic acid sequences for CRBN polypeptides from other species can be obtained from GenBank® by performing standard sequence searches (e.g., BLAST searches) using one or more of the above listed sequences (e.g., a human CRBN amino acid or nucleic acid sequence).

Any appropriate method can be used to determine the level of CRBN mRNA or CRBN polypeptide present within cancer cells. For example, RT-PCR, quantitative PCR, Northern blotting and gene expression profiling techniques can be used to assess CRBN mRNA levels. In some cases, ELISAs, immunocytochemistry, flow cytometry, Western blotting, proteomic, and mass spectrometry techniques can be used to assess CRBN polypeptide levels. Any appropriate sample containing cancer cells can be obtained and assessed for CRBN expression. For example, fine-needle aspiration biopsies, surgical tissue biopsies, or blood samples can be obtained, and the level of CRBN expression within the cancer cells of such samples can be determined as described herein.

The term "elevated level" as used herein with respect to the level of CRBN expression can be in comparison with the median CRBN expression level present in normal non-cancer cells of the same cell type of the cancer to be assessed (e.g., the median CRBN expression level determined from a random sampling of 5, 10, 15, 20, 30, 40, 50, 100, 500, or more non-cancer cell samples from humans known not to have cancer). In such cases, the presence of an elevated level can indicate that the patient's cancer cells are susceptible to treatment with lenalidomide, thalidomide, and/or other IMiDs, while the absence of such an elevated level can indicate that the patient's cancer cells are not susceptible to treatment with lenalidomide, thalidomide, or other IMiDs.

This document also provides methods and materials to assist medical or research professionals in determining if cancer cells (e.g., multiple myeloma cells) are susceptible or resistant to treatment with lenalidomide, thalidomide, and/or other IMiDs. Medical professionals can be, for example, doctors, nurses, medical laboratory technologists, and pharmacists. Research professionals can be, for example, principal investigators, research technicians, postdoctoral trainees, and graduate students. A professional can be assisted by (1) determining the level of CRBN expression in cancer cells as described herein, and (2) communicating information about the CRBN expression level to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

CRBN is Required for the Anti-myeloma Activity of Thalidomide, Lenalidomide, and Pomalidomide Cell Lines, Compounds, siRNA, Plasmids, and Reagents Myeloma cell lines were maintained in RPMI 1640, supplemented with 10% FCS and antibiotics. Lentiviral shRNA clones targeting human CRBN and non-targeting (NT) control lentiviral constructs were obtained from Sigma-Aldrich (St. Louis, Mo.). Anti-Flag and anti-DDB1 antibodies were obtained from Cell Signaling Technology (Danvers, Mass.). Lipofectamin™ 2000 was obtained from Invitrogen (Carlsbad, Calif.). Annexin V apoptosis detection kit was obtained from BD Biosciences (San Jose, Calif.). Lenalidomide was obtained commercially.

CRBN shRNA Lentiviral Experiments

The lentiviruses expressing NT or CRBN shRNAs were subcloned into a GFP containing construct and used to infect various myeloma cell lines as described elsewhere (Zhu et al., *Blood*, 117(14):3847-3857 (2011); Epublished Feb. 2, 2011). After a 48-hour infection period, efficiency was measured at 72 hours and 6 days post infection by FACScan analysis of GFP expression. Cell viability was measured by 3-(4,5-dimethylthiazol)-2,5-diphenyl tetrazolium (MTT) dye absorbance according to the manufacturer's instructions (Boehringer Mannheim, Mannheim, Germany). Cells were also harvested at 72 hours post infection for real-time PCR analysis of CRBN levels in control and CRBN shRNA expressing cells. At three weeks post infection, GFP-positive cells were sorted and expanded. Real-time PCR was performed to measure CRBN levels in sorted cells.

In some experiments, cells were incubated with various doses of lenalidomide, dexamethasone, melphalan, or bortezomib. Plates were incubated for 72 hours to six days. Cell viability was determined using an MTT assay. Each experimental condition was performed in triplicate and repeated at least once.

Real-time PCR

Total RNA was isolated using RNeasy Plus Mini kit (Qiagen) and reverse transcribed using QuantiTect Reverse Transcription kit (Qiagen). The Quantitative PCR were performed using TaqMan Universal PCR Master Mix with pre-designed probes (Applied Biosystems, Foster City, Calif.), and the comparative $C_T$ method was used for relative quantification on an ABI 7900HT Fast Real-Time PCR system (Applied Biosystems, Foster City, Calif.).

Gene Expression Profile Analysis

Myeloma cells infected with NT or CRBN shRNA expressing lentiviruses were harvested, and total RNA was prepared using RNeasy Plus Mini Kit (Qiagen). The gene expression profiles (GEP) were generated from total RNA labeled using the Affymetrix OneStep IVT labeling procedure and hybridized to the Affymetrix U133Plus2.0 genechip. All labeling, hybridization, washing, and scanning steps were performed following the manufacturer's recommended protocol by a MicroArray facility. The CEL files were processed and normalized by MAPP application with the following default settings: BG Correction: gcrma; Normalization: fastlo; PM Correction: affinities only; Summarization: medianpolish; and computeCalls: TRUE. Differential expression between the treatment samples and the controls were selected using |FC|>2 to filter the genes for each comparison.

Immunoblotting

Western Blotting was performed. Briefly, equal amounts of protein were subjected to SDS-PAGE gel electrophoreses followed by transfer to PVDF membranes. Membranes were probed with primary antibodies overnight and then washed and incubated with HRP-conjugated-secondary antibodies. Detection was performed by the Enhanced Chemical Luminescence (ECL) method. The membranes were stripped and re-probed with anti-β-actin antibodies to confirm protein loading.

Array Comparative Genomic Hybridization

Genomic DNA was obtained using Puregene blood kit (Qiagen; Valencia, Calif.) according to the manufacturer's recommendations. High-resolution array-based comparative genomic hybridization (aCGH) was performed with the Human Genome 244A microarray (Agilent Technologies; Palo Alto, Calif.). DNA samples from a pool of nine female human lymphoblastoid cell lines (obtained from the Coriell repository) were used as the normal reference in the hybridization experiments. The digesting, labeling, and hybridizing steps were performed as described elsewhere with minor modifications (Braggio et al., *Cancer Res.*, 69(8):3579-88 (2009)). Briefly, 1.2 μg of tumor and reference DNAs were separately digested with Bovine DNaseI (Ambion; Austin, Tex.) for 12 minutes at room temperature. Next, random primers and exo-Klenow fragment (Invitrogen; Carlsbad, Calif.) were used to differentially label tumor (Cy5) and reference (Cy3) genomic DNA samples (GE Healthcare; Piscataway, N.J.). Labeled genomic reactions were cleaned-up with purification columns (Invitrogen) and hybridized at 65° C. for 40 hours. Microarrays were scanned in a DNA Microarray Scanner (Agilent Technologies). Feature extraction was performed with Feature extraction Software, version 9.5 (Agilent Technologies). Log 2 ratio data were imported and analyzed using DNA Analytics software version 4.0.85 (Agilent Technologies).

Copy-number abnormalities (CNA) were calculated using aberration detection module (ADM)-1 algorithm (Lipson et al., *J. Comput. Biol.*, 13:215-28 (2006)) with a threshold of 7.5. 2 probe, 0.25 log 2 filters were used in the aberration detection, obtaining an average genomic resolution of 17 Kb.

Results

Myeloma Cell Responsiveness to IMiDs in vitro

The baseline cytotoxicity of thalidomide and lenalidomide was established. A MTT assay was performed on a panel of genetically heterogeneous human MM cells lines in vitro (FIG. 1). Lenalidomide inhibited growth of 8 of 11 tested MM cell lines at the concentration between 1.6 μM to 50 μM in vitro (FIG. 1). The same dose of thalidomide, however, had no effect on MM cell growth.

Suppression of Cereblon is Cytotoxic

Figure 2:
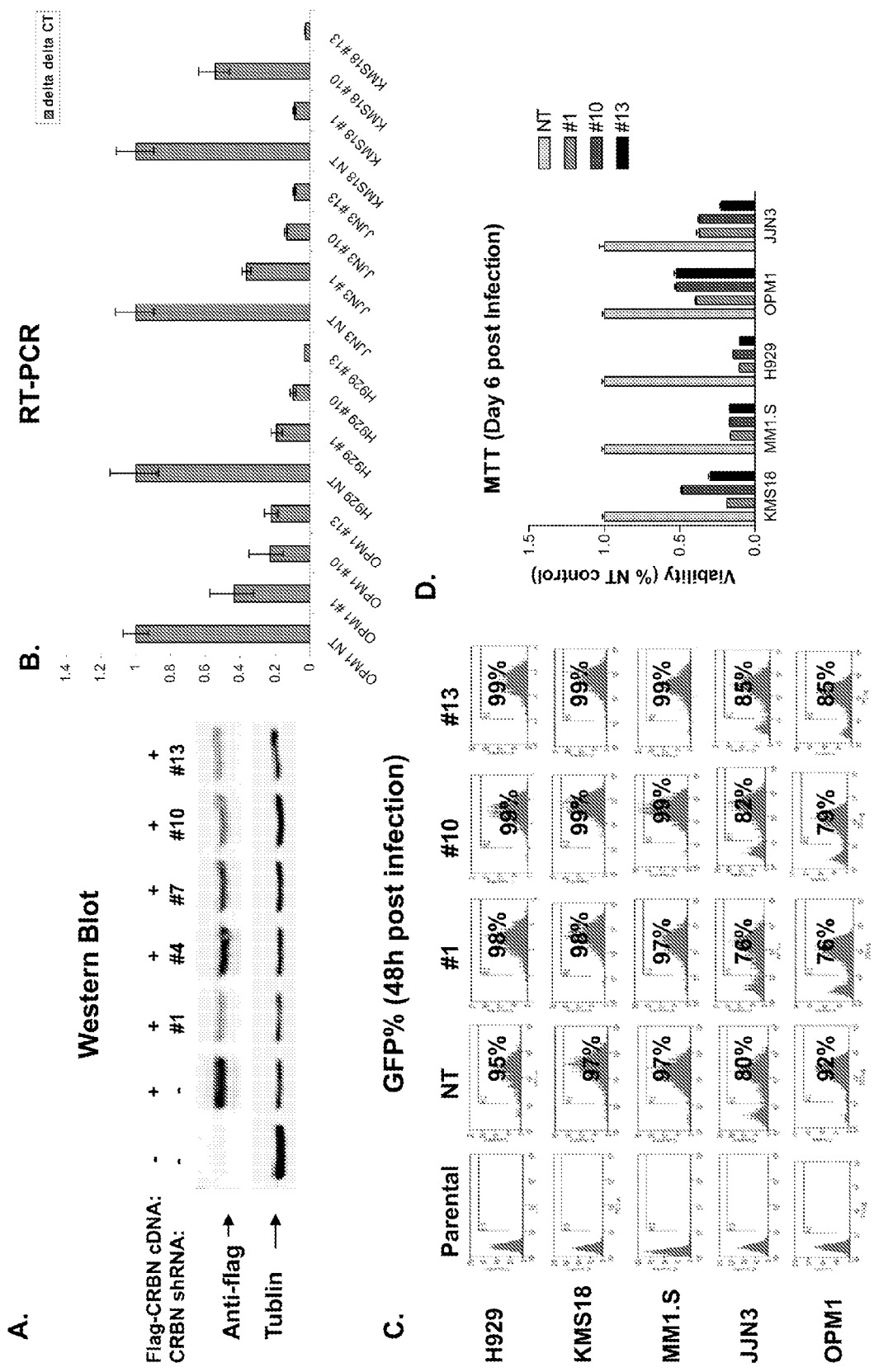
FIG. 2A is a photograph of a Western Blot of proteins obtained from 293 cells expressing a FLAG-CRBN construct with or without an shRNA designed to reduce CRBN expression probed with either an anti-FLAG antibody or anti-tublin antibody. A negative control included cells not expressing the FLAG-CRBN cDNA and not containing an shRNA.
FIG. 2B is a graph plotting RT-PCR determined CRBN expression levels for cells containing non-targeting control shRNA (NT) or an shRNA designed to reduce CRBN expression (#1, #10, or #13). Each shRNA construct included a sequence encoding GFP.
FIG. 2C contains graphs plotting the percentage of GFP from the indicated cell lines containing non-targeting control shRNA (NT) or an shRNA designed to reduce CRBN expression (#1, #10, or #13).
FIG. 2D is a graph plotting viability of the indicated cell lines six days post infection with viruses containing non-targeting control shRNA (NT) or an shRNA designed to reduce CRBN expression (#1, #10, or #13).
Figure 4:
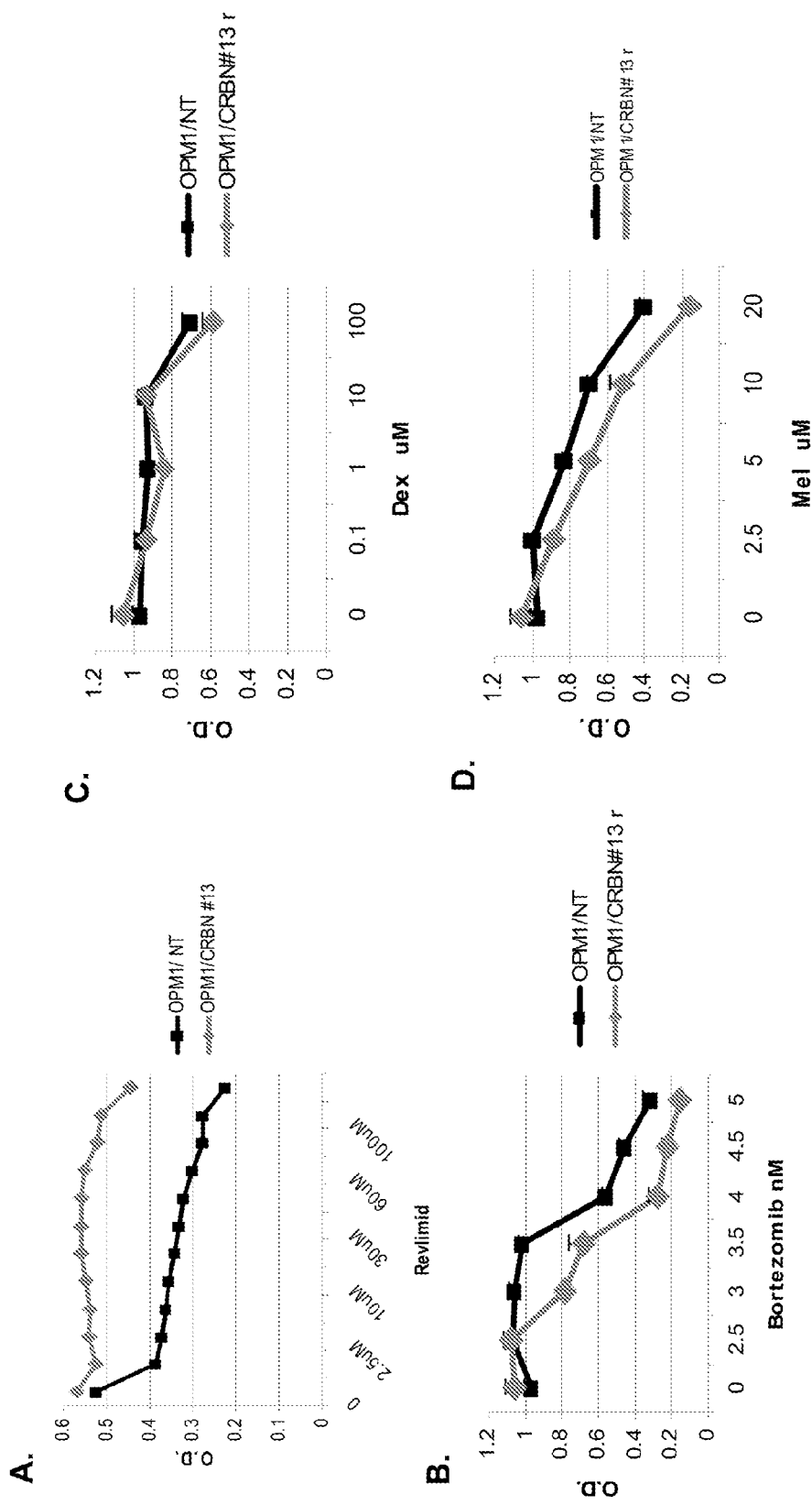
FIG. 4A is a graph plotting cell viability (O.D.) for OPM1 (myeloma) cells containing either a non-targeting control shRNA (NT) or shRNA #13 and treated with the indicated amount of revlimid.
FIG. 4B is a graph plotting cell viability (O.D.) for OPM1 cells containing either a non-targeting control shRNA (NT) or shRNA #13 and treated with the indicated amount of bortezomib.
FIG. 4C is a graph plotting cell viability (O.D.) for OPM1 cells containing either a non-targeting control shRNA (NT) or shRNA #13 and treated with the indicated amount of dexamethasone.
FIG. 4D is a graph plotting cell viability (O.D.) for OPM1 cells containing either a non-targeting control shRNA (NT) or shRNA #13 and treated with the indicated amount of melphalan.

Lentiviral CRBN shRNAs were introduced into myeloma cell lines, and the effects of silencing CRBN on myeloma cell viability were measured. Five pre-designed CRBN shRNA lentiviral expression constructs were obtained. Three of the five exhibited a knockdown of CRBN expression using a Flag-tagged CRBN in 293 cells as the target (FIG. 2A). The lentiviruses expressing these three CRBN shRNAs and lentiviruses expressing non-targeting (NT) control shRNAs were used to infect myeloma cell lines. At 48 hours post infection, the infection efficiency of each virus on different cell lines was measured by FACScan analysis of GFP positive cells (FIG. 2B). Knock-down CRBN expression and cell viability were further measured at day 3 and day 6 post infection by RT-PCR and MTT, respectively. As shown in FIGS. 2C and 2D, MM cell lines infected with CRBN shRNAs exhibited reduced CRBN expression and cell viability as compared with control virus infected cells.

Suppression of Cereblon Confers Lenalidomide Resistance

Although a mean of 70% myeloma cells stopped growing or died after knock-down of CRBN by day 6 post infection, a percentage of infected cells was found to survive. After sorting these cells by GFP expression, CRBN knock-down in those cells was still observed by real-time PCR (FIGS. 3A and 3B), suggesting that a non CRBN-dependent survival pathway(s) may exist. Proliferation of those CRBN depleted but surviving MM cells were then tested in the absence or presence of different anti-myeloma drugs. As shown in FIG. 3C, three different myeloma cell lines, which had more than 98% GFP positive cells and substantial CRBN knock-down, demonstrated acquired resistant to lenalidomide when compared with their NT control cells. Most of those cell lines exhibited resistance to both lenalidomide and pomalidomide, but exhibited similar sensitivity to melphalan and dexmethason. In some cases, some cell lines became more sensitive to Bortezomib after CRBN silencing (FIGS. 4A-D). These results demonstrate a requirement of CRBN for the activity of these IMiDs.

Molecular Basis of Drug Resistance After CRBN Knock-down and Effects of CRBN Silencing In order to determine the molecular basis of drug resistance after CRBN knock-down, a gene expression profile (GEP) analysis was performed on OPM1 cells which stably express NT or CRBN shRNA after lenalidomide treatment for 48 hours. Compared with NT controls (i.e., lenalidomide responsive cells, which exhibited about six hundred genes up or down regulated after 48 hours lenalidomide treatment), CRBN depleted and thus lenalidomide resistant cells only exhibited 30 genes down regulated (3% of control) and 150 genes (24% of control) up-regulated after treatment, further demonstrating that CRBN is involved in a full complement drug response.

Figure 5:
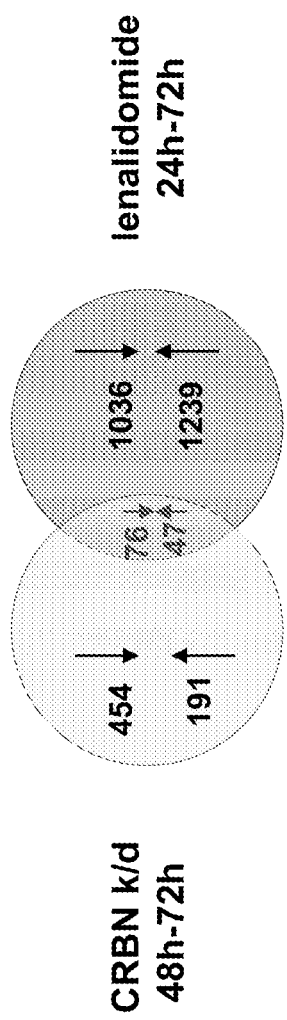
FIG. 5 is a diagram showing the overlap between up- and down-regulated genes for cells treated with shRNAs to reduce CRBN expression and cells treated with lenalidomide.

In order to know whether knock-down of CRBN induces the same effects on gene expression as lenalidomide treatment, a GEP analysis was performed on OPM1 cells either treated with lenalidomide for 24, 48, or 72 hours or transfected with CRBN shRNA for 48 or 72 hours. A comparison of the profile induced by lenalidomide alone versus the profile induced by CRBN knockdown alone was performed. Only 123 genes were found to have shared GEP changes between the two groups (FIGS. 5 and 8). A pathway analysis indicated that those genes are enriched on cell survival and immune response cell signaling and regulated by several transcription factors such as c-myc, Sp1, and P53.

Genomic Deletion of Cereblon Confers IMiD Resistance in Cell Lines

Figure 6:
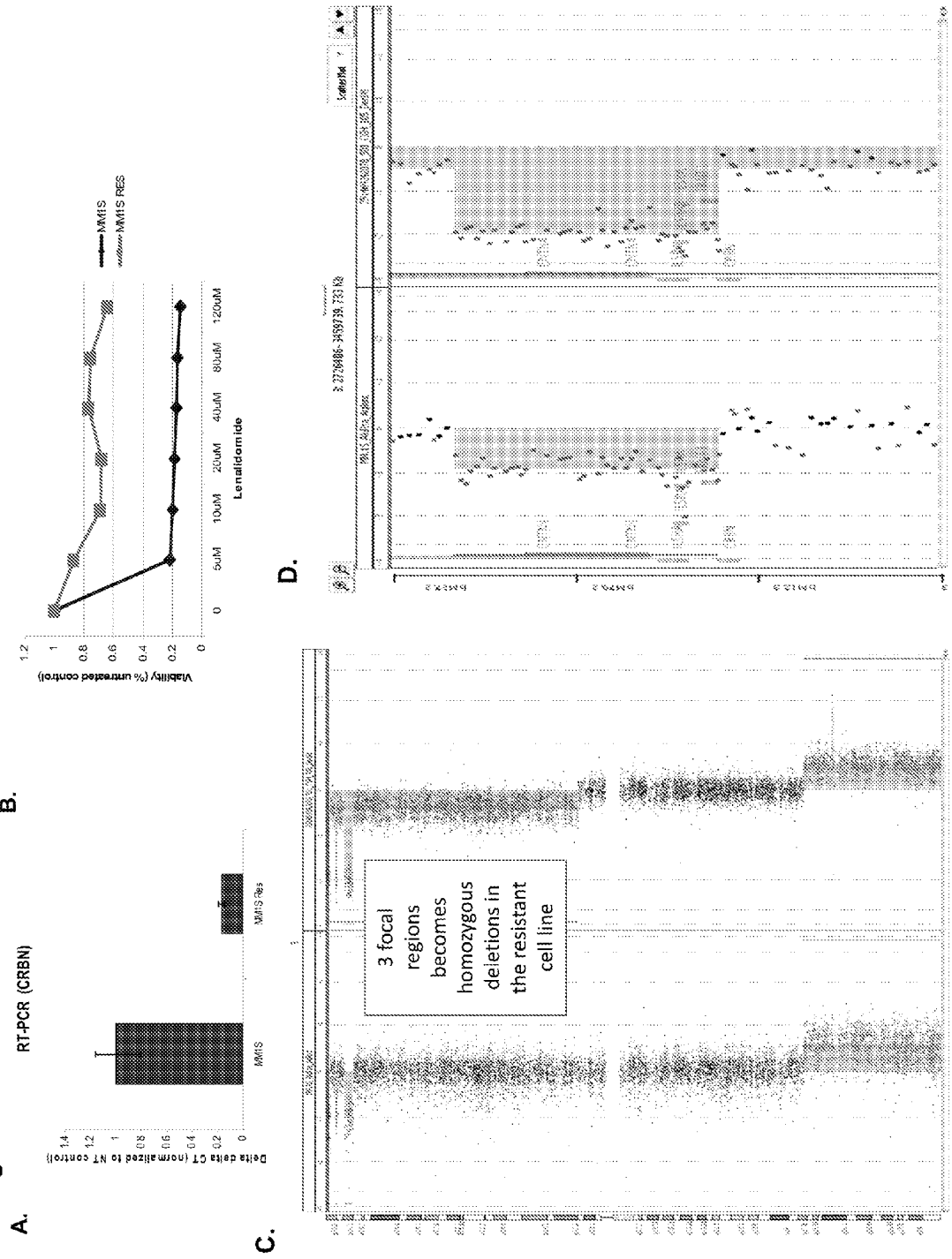
FIG. 6A is a graph plotting RT-PCR expression of CRBN for MM1S cells and MM1s res cells. MM1s res cells were generated to be lenalidomide resistant in the laboratory.
FIG. 6B is a graph plotting cell viability of MM1S cells and MM1s res cells treated with the indicated amounts of lenalidomide.
FIG. 6C shows 3 regions on chromosome arm 3p that have an additional deletion in MM1S lenalidomide resistant cell line (right plot) compared with MM1S lenalidomide sensitive cell line (left plot).
FIG. 6D is a gene plot that confirms that one of the chromosomal regions in MMIs lenalidomide resistant cells shown in FIG. 6C includes the 3' portion of CRBN.
Figure 7:
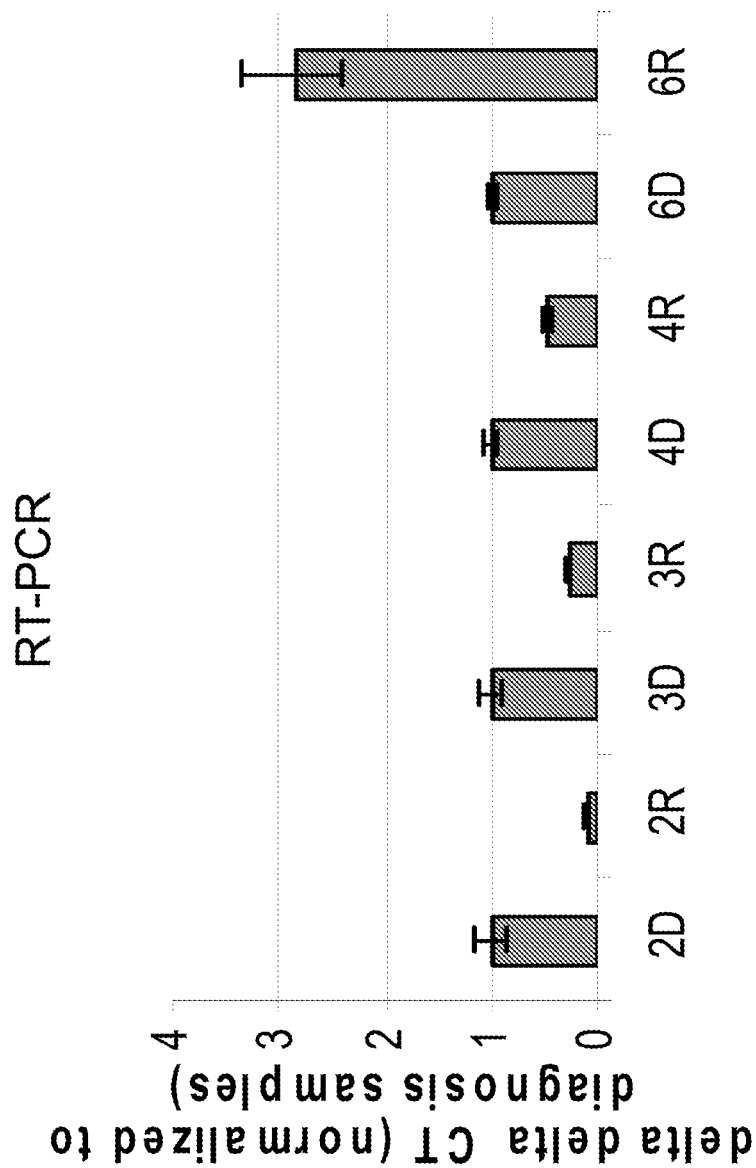
FIG. 7 is a graph plotting RT-PCR for CRBN in matched patient samples before and after exposure to lenalidomide.

To determine whether down-regulation of CRBN also exists in a lenalidomide resistant MM1.S cell line (MM1.S res; a gift from Dr. Orlwoski), which was generated by culturing MM1.S cells in gradually increasing concentrations of lenalidomide, RT-PCR was performed to quantitate CRBN levels in parental MM1.S cells and MM1.S res cells. Compared with parental MM1.S cells, lenalidomide resistant cells exhibited much lower levels of CRBN expression (FIG. 6A). An array CGH analysis was performed using the isogenic cell lines MM1.S and MM1.S res to identify the genetic basis for why CRBN is down-regulated in the resistant cell line. A mono-allelic deletion of CRBN was noted in MM1.S, which becomes bi-allelic in MM1.S res. This confirms a requirement for CRBN in lenalidomide activity.

Lenalidomide Refractory Patients Demonstrate Low Cereblon Levels Post Treatment

Since CRBN was determined to be required for lenalidomide and pomalidomide response, the following was performed to investigate whether lenalidomide resistance in MM is the result of lower levels of CRBN in patients. In three patients for which pre- and post-treatment samples were available, CRBN expression levels were assessed using RT-PCR. The expression of CRBN in MM cells from samples obtained from three patients who relapsed was lower than the levels measured in their samples collected at diagnosis stage. These RT-PCR results are consistent with mRNA sequencing analysis data.

The results provided herein demonstrate a requirement for IMiDs to bind CRBN in order to be effective and demonstrate that loss of CRBN function confers resistance to the IMiD class of drugs. Gene expression changes induced by lenalidomide exposure were to a large extent vanquished when CRBN was depleted. Interestingly, depleting CRBN is directly cytotoxic to MM cells, further implicating CRBN as a mediator of IMiD function. In patients exposed to and resistant to lenalidomide, CRBN levels appear to decline. Thus, the presence of CRBN can be a requirement for activity of this drug class and while its consequent suppression mediates cell death, its complete loss renders the drug class ineffective.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating refractory myeloma, wherein said method comprises:
    (a) administering thalidomide, lenalidomide, or pomalidomide to a mammal having myeloma, wherein said myeloma of said mammal develops a resistance to said thalidomide, lenalidomide, or pomalidomide following said administering step,
    (b) determining that myeloma cells obtained from said mammal following said administering of step (a) lack an elevated level of CRBN expression, and
    (c) administering Bortezomib, an alkylating agent, or a corticosteroid to said mammal.

2. The method of claim 1, wherein said method comprises administering lenalidomide in step (a).

3. The method of claim 1, wherein said method comprises administering thalidomide in step (a).

4. The method of claim 1, wherein said method comprises administering pomalidomide in step (a).

5. The method of claim 1, wherein said method comprises administering said Bortezomib in step (c).

6. The method of claim 1, wherein said method comprises administering said alkylating agent in step (c).

7. The method of claim 1, wherein said method comprises administering said corticosteroid in step (c).

* * * * *